United States Patent [19]

Cantello

[11] 4,250,173
[45] Feb. 10, 1981

[54] HETEROCYCLIC COMPOUNDS AND PHARMACEUTICAL USE

[75] Inventor: Barrie C. C. Cantello, Redhill, England

[73] Assignee: Beecham Group Limited, England

[21] Appl. No.: 94,100

[22] Filed: Nov. 14, 1979

[30] Foreign Application Priority Data

Nov. 29, 1978 [GB] United Kingdom ............... 46531/78
May 15, 1979 [GB] United Kingdom ............... 15737/79

[51] Int. Cl.³ .................. A61K 31/42; A61K 31/425;
A61K 31/535; A61K 31/54; C07D 263/28;
C07D 265/08; C07D 277/18; C07D 279/06

[52] U.S. Cl. ............................. 424/246; 424/248.51;
424/248.53; 424/248.55; 424/248.56; 424/250;
424/267; 424/270; 424/272; 544/53; 544/54;
544/55; 544/58.4; 544/58.5; 544/58.6;
544/58.7; 544/60; 544/88; 544/96; 544/133;
544/137; 544/369; 546/209; 548/146; 548/194;
548/198; 548/233

[58] Field of Search ...................... 544/58.6, 58.7, 60,
544/53, 54, 55, 133, 137, 88, 96, 58.5, 58.4, 369;
546/209; 548/146, 194, 198, 233; 424/246,
248.51, 248.53, 248.55, 248.56, 250, 267, 270, 272

[56] References Cited

FOREIGN PATENT DOCUMENTS 852565 9/1977 Belgium .

OTHER PUBLICATIONS

Tutwiler et al., Diabetes, vol. 27, (1978). pp. 856 and 868.

*Primary Examiner*—Richard Ramond
*Attorney, Agent, or Firm*—Jacobs & Jacobs

[57] ABSTRACT

A compound, with hypolgycaemic activity, having formula (II) or a pharmaceutically acceptable quaternary ammonium or acid addition salt thereof:

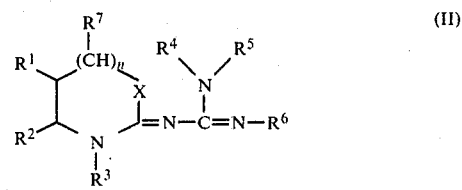

(II)

wherein X represents oxygen or sulphur;
$n_7$ represents zero or 1;
$R^7$ represents hydrogen or $C_{1-6}$ alkyl;
$R^1$ and $R^2$ are the same or different and represent hydrogen, $C_{1-6}$ alkyl, phenyl, benzyl, or $C_{3-6}$ cycloalkyl;
$R^3$ represents hydrogen, $C_{1-6}$ alkyl, phenyl or benzyl;
$R^4$ represents hydrogen or $C_{1-6}$ alkyl;
$R^5$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^4$ and $R^5$ together represent the remaining members of a 5- or 6-membered ring optionally containing an oxygen, sulphur or additional nitrogen atom and being optionally substituted with $C_{1-6}$ alkyl, carboxy or $C_{1-6}$ alkoxycarbonyl; and
$R^6$ represents phenyl, optionally substituted with up to 3 groups selected from halogen, $C_{1-6}$ alkyl, $C_{1-6}$ alkoxy, $C_{1-6}$ alkanoyl, $C_{1-6}$ alkanoyloxy, nitro, hydroxy, amino, substituted amino, carboxy, and $C_{1-6}$ alkoxycarbonyl.

17 Claims, No Drawings

HETEROCYCLIC COMPOUNDS AND PHARMACEUTICAL USE

This invention relates to a class of novel heterocyclic compounds which are useful in the treatment of diabetes. The invention also relates to a process for their preparation and to pharmaceutical compositions containing them.

The compound of formula (I):

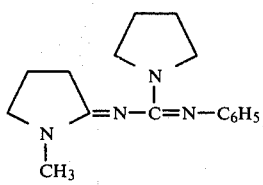

has been reported to be useful in the treatment of diabetes in Belgian Pat. No. 852,565 and in Diabetes, 27, 856 and 868 (1978).

We have now found a class of heterocyclic imine compounds which have hypoglycaemic activity.

Accordingly the present invention provides a compound of formula (II) or a pharmaceutically acceptable quaternary ammonium or acid addition salt thereof:

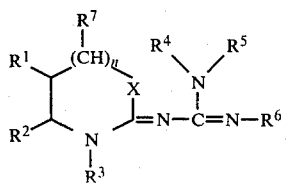

wherein
X represents oxygen or sulphur;
n represents zero or 1;
$R^7$ represents hydrogen or $C_{1-6}$ alkyl;
$R^1$ and $R^2$ are the same or different and represent hydrogen, $C_{1-6}$ alkyl, phenyl, benzyl, or $C_{3-6}$ cycloalkyl;
$R^3$ represents hydrogen, $C_{1-6}$ alkyl, phenyl or benzyl;
$R^4$ represents hydrogen or $C_{1-6}$ alkyl;
$R^5$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^4$ and $R^5$ together represent the remaining members of a 5- or 6-membered ring optionally containing an oxygen, sulphur or additional nitrogen atom and being optionally substituted with $C_{1-6}$ alkyl, carboxy or $C_{1-6}$ alkoxycarbonyl; and
$R^6$ represents phenyl, optionally substituted with up to 3 groups selected from halogen, $C_{1-6}$ alkyl, $C_{1-6}$ alkoxy, $C_{1-6}$ alkanoyl, $C_{1-6}$ alkanoyloxy, nitro, hydroxy, amino, substituted amino, carboxy, and $C_{1-6}$ alkoxycarbonyl.

Suitable quaternary salts of compound (II) include $C_{1-6}$ alkyl halides, di-$C_{1-6}$ alkyl sulphates, and benzyl halides.

Preferred quaternary salts are the $C_{1-6}$ alkyl halides; in particular the methylhalide, such as the methyliodide salt.

Suitable acid addition salts of compound (II) include inorganic salts such as the sulphate, nitrate, phosphate and borate, hydrohalides such as the hydrochloride, hydrobromide and hydroiodide, and organic acid addition salts such as acetate, oxalate, tartrate, maleate, citrate, succinate, benzoate, ascorbate, methanesulphonate and p-toluenesulphonate.

Preferred salts are hydrohalide salts.

The group X in compounds of formula (II) preferably represents sulphur and n is preferably zero.

Examples of suitable $C_{1-6}$ alkyl groups which $R^1$ to $R^5$ and $R^7$ may represent include methyl, ethyl, n- and isopropyl, and n-, sec-, iso-, and tert-butyl.

Examples of cycloalkyl groups which $R^1$ and $R^2$ may represent include cyclopentyl and cyclohexyl.

Suitable substitutents for the phenyl and benzyl groups for $R^5$ and the phenyl group for $R^6$ include ortho-, meta- and para-methyl, methoxy, chloro and bromo.

Preferably n is zero.

Suitably $R^1$, $R^2$ and $R^7$ represent hydrogen, methyl, ethyl, or n-propyl. Preferably $R^1$ and $R^2$ are both hydrogen. When n is 1, then preferably $R^7$ is hydrogen.

Suitably $R^3$ is methyl, ethyl, n-propyl, or phenyl. Advantageously $R^3$ represents hydrogen or $C_{1-6}$ alkyl, especially methyl or ethyl.

Suitably $R^4$ is hydrogen, methyl, ethyl or n-propyl, and $R^5$ represents methyl, ethyl, n-propyl, phenyl or benzyl. When $R^4$ and $R^5$ complete a ring, suitable such rings include pyrrolidine, piperidine, morpholine, thiomorpholine, piperazine and 4-($C_{1-6}$ alkyl)piperazine, for example 4-methylpiperazine rings.

Suitably $R^6$ is phenyl.

One sub-group of compounds falling within the scope of this invention comprises compounds of formula (III) and pharmaceutically acceptable quaternary and acid addition salts thereof:

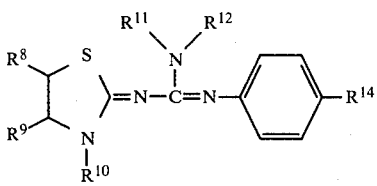

wherein
$R^8$ and $R^9$ represent hydrogen or $C_{1-6}$ alkyl;
$R^{10}$ represents hydrogen or $C_{1-6}$ alkyl;
$R^{11}$ and $R^{12}$ together represent the remaining members of a 5- or 6-membered ring optionally containing an oxygen or additional nitrogen atom and being optionally substituted with $C_{1-6}$ alkyl; and
$R^{14}$ represents hydrogen, $C_{1-6}$ alkyl or halogen.

Compounds of formula (II) include the following:
N-(3-methylthiazolidin-2-ylidene)-N'-phenyl-1-pyrrolidine carboxamidine;
N-(3-methylthiazolidin-2-ylidene)-N'-phenyl-1-piperidine carboxamidine;
N-(3-methylthiazolidin-2-ylidene)-N'-phenyl-1-(4-methylpiperazine)carboxamidine;
N-(3-methylthiazolidin-2-ylidene)-N'-phenyl-1-morpholine carboxamidine;
N'-(4-methylphenyl)-N-(3-methylthiazolidin-2-ylidene)-1-pyrrolidine carboxamidine;
N'-(4-chlorophenyl)-N-(3-methylthiazolidin-2-ylidene)-1-pyrrolidine carboxamidine;

N-(3-ethylthiazolidin-2-ylidene)-N'-phenyl-1-pyrrolidine carboxamidine;

N-(3-methylthiazolidin-2-ylidene)-N'-phenyl-1-thiomorpholine carboxamidine;

N'-(4-chlorophenyl)-N-(3-methylthiazolidin-2-ylidene)-1-morpholine carboxamidine;

N'-(4-bromophenyl)-N-(3-methylthiazolidin-2-ylidene)-1-morpholine-carboxamidine;

N'-(3,4-dichlorophenyl)-N-(3-methylthiazolidin-2-ylidene)-1-pyrrolidine carboxamidine;

N,N-diethyl-N'-(3-methylthiazolidin-2-ylidene)-N''-phenylguanidine;

N'-(2,6-dichlorophenyl)-N-(3-methylthiazolidin-2-ylidene)-1-morpholine-carboxamidine;

N-(3-methyloxazolidin-2-ylidene)-N'-phenyl-1-pyrrolidine carboxamidine.

Compounds of formula (II) may be prepared by reacting a compound of formula (IV) or a salt thereof;

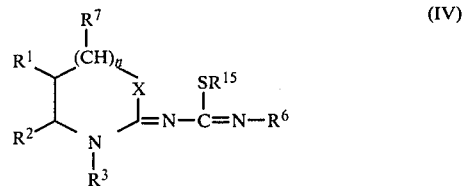

wherein $R^1$, $R^2$, $R^3$, $R^6$, $R^7$, n and X are as defined with respect to formula (II) above and $R^{15}$ represents $C_{1-6}$ alkyl; with an amine of formula $R^4R^5NH$, wherein $R^4$ and $R^5$ are as defined with reference to formula (II) above and thereafter where desired converting a free base of formula (II) so obtained into a pharmaceutically acceptable salt or converting a salt of a compound of formula (II) so obtained into the free base.

The reaction is conveniently carried out in polar organic solvent, the choice of which is not critical to the success of the reaction provided that it forms a homogeneous solution of the reagent and is substantially inert to the reagent and product. It has been found that lower alkanols such as iso-propanol are particularly convenient.

The reaction is generally carried out at a moderate temperature i.e. greater than room temperature, the reflux temperature of the solvent being selected for convenience.

The period for which the reaction is allowed to proceed depends upon the particular starting materials employed. The course of the reaction may be followed by conventional methods such as thin layer chromatography and terminated when an optimum quantity of product is present in the reaction mixture. However, in general we have found that it is convenient to leave the reaction mixture to reflux overnight.

Intermediates of general formula (IV) are novel and represent a further aspect of the invention.

Example of lower alkyl groups which $R^{15}$ may represent include methyl, ethyl, n-propyl or n-butyl but preferably $R^{15}$ represents methyl.

The intermediates of formula (IV) may be prepared by the route shown in the following scheme:

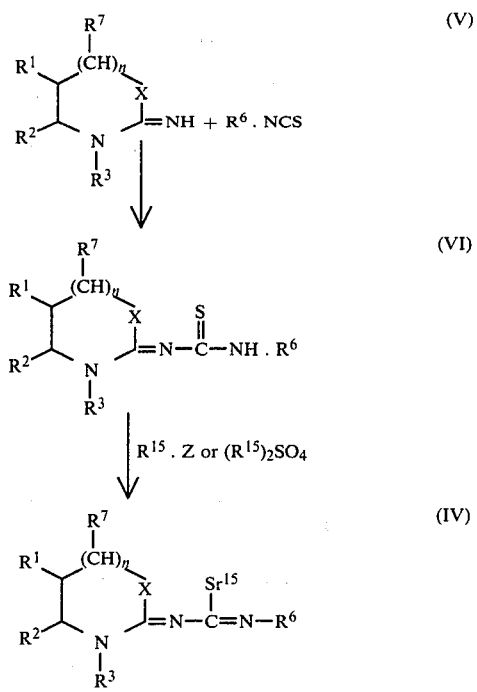

Thus, intermediates (IV) are prepared by alkylation of a thiourea (VI) using an alkylating agent $R^{15}.Z$ or $(R^{15})_2SO_4$ wherein $R^{15}$ is as defined with reference to formula (IV) and Z is a leaving group such as chloride, bromide or iodide. Suitably the reaction is carried out in a polar organic solvent, the choice of which is not critical provided that the solvent is substantially inert to the reagents and product. Suitable solvents include lower alkanones and alcohols. The reaction is suitably carried out at the boiling point of the solvent.

The thiourea (VI) is in turn prepared by reacting an iso-thiocyanate $R^6.NCS$ with a corresponding imino compound (V), where $R^1$, $R^2$, $R^3$, $R^6$, $R^7$, n and X are as defined with reference to formula (II). This reaction is carried out in a solvent such as toluene, benzene, dioxane, tetrahydrofuran, methanol or ethanol. The reaction is carried out at non-extreme temperatures, i.e. up to and including the reflux temperature of the solvent.

Compounds of formula (II) may also be prepared by reacting a compund of formula (VII).

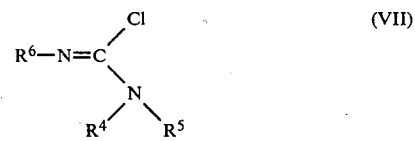

wherein $R^4$, $R^5$ and $R^6$ are as defined with respect to formula (II) above; with an imino compound (V), where $R^1$, $R^2$, $R^3$, $R^7$, n and X are as defined with respect to formula (II) above and thereafter where desired converting a free base of formula (II) so obtained into a pharmaceutically acceptable salt or converting a salt of a compound of formula (II) so obtained into the free base.

The reaction is conveniently carried out in a nonhydroxylic solvent system such as an ether, chlorinated hydrocarbon or a mixture thereof. Suitable solvent systems include mixtures of diethyl ether and chloroform. The reaction is suitably carried out at ambient temperature. The period for which the reaction is allowed to proceed may be determined by methods as described hereinbefore; however, we have found it convenient to leave the reaction mixture to stand overnight.

The intermediates of formula (VII) may be prepared by reaction of an isocyanide dichloride of formula: $R^6-N=CCl_2$ wherein $R^6$ is as defined with respect to formual (II) above; with an amine of formula $R^4R^5NH$, wherein $R^4$ and $R^5$ are as defined with reference to formula (II) above. Suitably the reaction is carried out in ethereal solvent such as diethyl ether of tetrahydrofuran. The reaction is suitably carried out at ambient temperature. The period for which the reaction is allowed to proceed may be determined by methods as described hereinbefore; however, we have found a two hour reaction time to be sufficient.

The quaternary ammonium salts of compounds of formula (II) may be prepared by reaction of the compounds of formula (II) with the corresponding quaternisation agent for example ($C_{1-6}$) alkyl, or benzyl halides such as methyl iodide, ethyl bromide, propyl bromide, or benzyl chloride, or sulphuric esters e.g. di($C_{1-6}$ alkyl)sulphates such as dimethyl sulphate or diethyl sulphate.

The quaternisation may be carried out in the presence or absence of a solvent, depending upon whether the quaternisation agent is or is not itself capable of acting as a solvent, at ambient temperature or under cooling, and under atmospheric pressure or under pressure in a sealed container. Organic solvents which are inert as regards the reaction and which are suitable for this purpose are ethers such as diethyl ether or tetrahydrofuran, hydrocarbons such as benzene or heptane, ketones such as acetone or butanone, and $C_{1-6}$ alkanols such as ethanol, propanol or butanol. The anionic function of the quaternary salt can readily be exchanged by a traditional ion exchange technique.

In order to put the compounds (II) to use as medicinal agents for the treatment of diabetes, they are presented as pharmaceutical compositions in a variety of dosage forms. This invention therefore also includes a pharmaceutical composition which comprises a compound of formula (II) together with a pharmaceutically acceptable carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example acacia, gelatin, sorbitol, tragacanth, or polyvinylpyrrolidone; fillers, for example calcium phosphate, sorbitol or glycine; tabletting lubricants, for example magnesium stearate, talc, polyethylene glycol, or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxy-methyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. The compounds may also if desired be incorporated in a foodstuff, for example in the form of a biscuit.

Suppositories will contain conventional suppository bases, e.g. cocoa butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. The dosage employed for adult treatment will of course depend on the dose-response characteristics of the particular active ingredient but will normally be in the range 0.5 to 150 mg/kg/day.

The following Examples illustrate the preparation of a number of compounds of this invention.

EXAMPLE 1

N-(3-methylthiazolidin-2-ylidene)-N'-phenyl-1-pyrrolidine carboxamidine hydroiodide (a)

1-(3-Methylthiazolidin-2-ylidene)-3-phenyl-2-thiourea

Sodium methoxide (2.16 g) was added to a mixture of 2-imino-3-methylthiazolidine hydroiodide (10.0 g) in ethanol (50 ml) and brought to reflux, with stirring. Phenylisothiocyanate (5.4 g) in ethanol (20 ml) was added to the mixture over 5 minutes and the resultant mixture heated under reflux, with stirring, for one hour then cooled in ice. Filteration gave analytically pure product, mpt 169°–170°, which may be recrystallised from isopropanol.

(b)

2-Methyl-3-(3-methylthiazolidin-2-ylidene)-1-phenyl-2-thiopseudourea hydroiodide A mixture of 1-(3-methylthiazolidin-2-ylidene)-3-phenyl-2-thiourea (2.30 g) and iodomethane (1.65 g) in acetone (75 ml) was heated under reflux for 45 minutes and evaporated to dryness in vacuo. The residue was triturated with acetone, diluted with ether and filtered. Recrystallisation of the resultant solid from iso-propanol gave the product mpt 158°–159°.

(c)

N-(3-Methylthiazolidin-2-ylidene)-N'-phenyl-1-pyrrolidine carboxamidine hydroiodide A mixture of 2-methyl-3-(3-methylthiazolidin-2-ylidene)-1-phenyl-2-thiopseudourea hydroiodide (4.0 g) and pyrrolidine (1.2 g) in iso-propanol (40 ml) was heated under reflux for 22 hours, cooled and diluted with diethyl ether. The precipitated solid was recrystallised from methanol-diethyl ether to give the product of analytical purity, mpt 157.5°–159°.

EXAMPLE 2

N-(3-Methylthiazolidin-2-ylidene)-N'-phenyl-1-piperidine carboxamidine

A mixture of 2-methyl-3-(3-methylthiazolidin-2-ylidene)-1-phenyl-2-thiopseudourea hydroiodide (2.0 g) and piperidine (1.0 g) in dry iso-propanol (20 ml) was heated under reflux for 37 hours, cooled, evaporated to dryness, aqueous sodium hydroxide added to the residue and extracted with diethyl ether (X 2). The combined organic extracts were washed with water, dried (MgSO$_4$), filtered and evaporated to dryness. Crystallisation of the residual gum from petroleum ether, bp 60°–80°, gave the analytically pure product, mpt 122.5°–123.5°.

EXAMPLE 3

N-(3-Methylthiazolidin-2-ylidene)-N'-phenyl-1-(4-methyl-piperazine) carboxamidine This product, mpt 112.5°–113.5°, (from petroleum ether, bp 60°–80°), was prepared by an analogous procedure to that described in Example 2, except that N-methylpiperazine was used in place of piperidine.

EXAMPLE 4

N-(3-Methylthiazolidin-2-ylidene)-N'-phenyl-1-morpholinecarboxamidine

This product, mpt 143°–145° after recrystallisation from ethyl acetate/petroleum ether, was obtained by an analogous procedure to that described in Example (2) except that morpholine was used in place of piperidine.

EXAMPLE 5

N'-(4-methylphenyl)-N-(3-methylthiazolidin-2-ylidene)-1-pyrrolidine carboxamidine hydroiodide This product, pmt 168°–169° (MeOH-ether), was prepared by an analogous procedure to that described in Example 1 via 3-(4-methylphenyl)-1-(3-methylthiazolidin-2-ylidene)-2-thiourea, mpt 161.5°–163°, and 2-methyl-1-(4-methylphenyl)-3-(3-methylthiazolidin-2-ylidene)-2-thiopseudourea hydroiodide, mpt 161°–163°.

EXAMPLE 6

N'-(4-chlorophenyl)-N-(3-methylthiazolidin-2-ylidene)-1-pyrrolidine carboxamidine This product, mpt 120°–121.5° (petroleum ether, b.p. 60°–80°) was obtained by an analogous procedure to that described in Example 2 (reaction time-48 hours). The precursors for this synthesis, 3-(4-chlorophenyl)-1-(3-methylthiazolidin-2-ylidene)-2-thiourea, mpt 177.5°–179°, and 2-methyl-1-(4-chlorophenyl)-3-(3-methylthiazolidin-2-ylidene)-2-thiopseudourea hydroiodide, mpt 124°–127° (CH$_3$OH-ether), were prepared by analogous procedures to that described in Examples (1a) and (1b) respectively.

EXAMPLE 7

N-(3-Ethylthiazolidin-2-ylidene)-N'-phenyl-1-pyrrolidine carboxamidine (a) 1-(3-Ethylthiazolidin-2-ylidene)-3-phenyl-2-thiourea Mpt 138°–140°, was prepared by an analogous procedure to that described in Example (1a).

(b)

2-Methyl-3-(3-ethylthiazolidin-2-ylidene)-1-phenyl-2-thiopseudourea hydroiodide

A mixture of 1-(3-ethylthiazolidin-2-ylidene)-3-phenyl-2-thiourea (4.0 g) and methyliodide (3.0 g) in acetone (100 ml) was heated under reflux for 45 minutes, cooled and evaporated to dryness. The residual gum was crystallised from CH$_3$OH-ether to give the analytically pure product, mpt 112°–114°.

(c)

N-(3-Ethylthiazolidin-2-ylidene)-N'-phenyl-1-pyrrolidine carboxamidine

Mpt 92.5°–93.5° (petroleum ether, bpt 60°–80°), was obtained by an analogous procedure to that described in Example 2 (reaction time—21 hours).

EXAMPLE 8

N-(3-Methylthiazolidin-2-ylidene)-N'-phenyl-1-thiomorpholine carboxamidine

The product, mpt 158°–160° after recrystallisation from ethyl acelate/petroleum ether (b.p. 60°–80°) was obtained by an analogous procedure to that described in Example (2), except that thiomorpholine was used in place of piperidine.

EXAMPLE 9

N'-(4-chlorophenyl)-N-(3-methylthiazolidin-2-ylidene)-1-morpholinecarboxamidine

This product, mpt 179°–181° after recrystallisation from ethyl acetate/petroleum ether (b.p. 60°–80°) was obtained by reaction of 2-methyl-1-(4-chlorophenyl)-3-(3-methylthiazolidin-2-ylidene)-2-thiopseudourea hydroiodide with morpholine by an analogous procedure to that described in Example (2).

EXAMPLE 10

N'-(4-Bromophenyl)-N-(3-methylthiazolidin-2-ylidene)-1-morpholine carboxamidine (a)

3-(4-bromophenyl)-1-(3-methylthiazolidin-2-ylidene)-2-thiourea

Mpt 179°–181°, was prepared by an analogous procedure to that described in Example (1a).

(b)

2-methyl-1-(4-bromophenyl)-3-(3-methylthiazolidin-2-ylidene)-2-thiopseudourea hydroiodide Mpt 158°–9° was prepared by an analogous procedure to that described in Example (1b).

(c)
N'-(4-bromophenyl)-N-(3-methylthiazolidin-2-ylidene)-1-morpholine carboxamidine Mpt 179°-82°, after recrystallisation from ethyl acetate/petroleum ether (bp 40°-60°) was obtained from 2-methyl-1-(4-bromophenyl)-3-[3-methylthiazolidin-2-ylidene)-2-thiopseudourea hydroiodide and morpholine by an analogous procedure to that described in Example (2).

EXAMPLE 11

N'-(3,4-dichlorophenyl)-N-(3-methylthiazolidin-2-ylidene)-1-pyrrolidinecarboxamidine (a)
3-(3,4-dichlorophenyl)-1-(3-methylthiazolidin-2-ylidene)-2-thiourea Mpt 146°-9°, was prepared by an analogous procedure to that described in Example (1a).

(b)
2-methyl-1-(3,4-dichlorophenyl)-3-(3-methylthiazolidin-2-ylidene)-2-thiopseudourea hydroiodide Mpt 130°-2°, was prepared by an analogous procedure to that described in Example (1b).

(c)
N'-(3,4-dichlorophenyl)-N-(3-methylthiazolidin-2-ylidene)-1-pyrrolidinecarboxamidine Mpt 89°-92°, after recrystallisation from petroleum ether (bp 40°-60°) was obtained from 2-methyl-1-(3,4-dichlorophenyl)-3-(3-methylthiazolidin-2-ylidene)-2-thiopseudourea hydroiodide by an analogous procedure to that described in Example (2).

EXAMPLE 12

N-(3-Methylthiazolidin-2-ylidene)-N'-phenyl-1-pyrrolidinecarboxamidine hydrochloride Pyrrolidine (1.5 g) in dry diethyl ether (10 ml) was added dropwise, at 0° C., with stirring to a solution of phenylisocyanide dichloride (1.7 g) in dry ether, the mixture stirred for two hours and filtered. To the filtrate, a solution of 2-imino-3-methylthiazolidine (2.3 g) in chloroform (50 ml) was added and the mixture allowed to stand overnight. Dilute sodium hydroxide solution was added and the mixture extracted with chloroform, the extracts washed with water, dried over anhydrous magnesium sulphate, filtered and the filtrate evaporated to dryness. The residue was dissolved in diethyl ether and dry hydrogen chloride gas passed through the solution. The solid obtained was recrystallised from methanol-diethyl ether to give the product, mpt 225°-7° of analytical purity.

EXAMPLES 13-15

By an analogous procedure to that described in Example 12 the following carboxamidines have been prepared by use of the appropriate imine, amine and isocyanide dichloride:

EXAMPLE 13

N,N-diethyl-N'-(3-methylthiazolidin-2-ylidene)-N''-phenyguanidine as an oil, purified by column chromatography on silica using 5% of (33% dimethylamine in IMS) in CH$_2$Cl$_2$ as eluent.

EXAMPLE 14

N'-(2,6-dichlorophenyl)-N-(3-methylthiazolidin-2-ylidene)-1-morpholinecarboxamidine, mpt 145°-7° (ethanol)

EXAMPLE 15

N-(3-methyloxazolidin-2-ylidene)-N'-phenyl-1-pyrrolidinecarboxamidine as an oil, purified by chromatography using 1% of (33% dimethylamine in 1MS) in CH$_2$Cl$_2$ as eluent.

EXAMPLE 16

N-(3-Methylthiazolidin-2-ylidene)-N'-phenyl-1-pyrrolidinecarboxamidine methiodide A mixture of N-(3-methylthiazolidin-2-ylidene)-N'-phenyl-1-pyrrolidine carboxamidine (generated from 0.7 g of its hydroiodide) and iodomethane (0.5 g) in toluene (50 ml) was allowed to stand at room temperature for two days. Filtration gave the desired methiodide salt of analytical purity, mpt 160°-2°.

EXAMPLE 17

N-(3-Methylthiazolidin-2-ylidene)-N'-phenyl-1-pyrrolidine-carboxamidine hydrochloride Sodium hydroxide (26 g) in water (115 ml) was added to a solution of N-(3-methylthiazolidin-2-ylidene)-N'-phenyl-1-pyrrolidine carboxamidine hydroiodide (208.2 g) in water (550 ml) stirred and extracted with diethyl ether ($\times$3). The combined organic extracts were washed with water, dried over anhydrous magnesium sulphate and filtered. Dry hydrogen chloride gas was bubbled through the filtrate and the solid obtained was recrystallised from isopropanol to give the product, mpt 227.5°-228°.

Biological Data

Activity on Glucose Tolerance in Fasted Mice

For this assay mice were fasted for 24 hours before the experiment and then randomised so that each treatment group contained 8 mice. The compounds were dosed orally in 1% aqueous carboxymethyl cellulose (10 ml/kg body weight), and 30 minutes later glucose (1 g/kg) was administered by the sub-cutaneous route. Blood samples for glucose analysis were taken from the tail 60 minutes after glucose administration; the results are shown in the table below.

N.B. A standard system for indicating the significance of results with respect to the controls (dose=zero mmol/kg) which received the 1% aqueous carboxymethyl cellulose vehicle only, is as follows:

TABLE

| Compound of Example No. | Dose of Compound (mmol/kg bodyweight) | Blood Glucose concentration (mmol/liter) 60 minutes after subcutaneous glucose load |
|---|---|---|
| 1 | 0 | 5.47 |
|   | 0.25 | 3.25**** |
| 2 | 0 | 5.81 |
|   | 0.25 | 3.20**** |
| 3 | 0 | 5.55 |
|   | 0.25 | 4.12** |
| 4 | 0 | 5.85 |
|   | 0.25 | 3.36**** |
| 5 | 0 | 5.81 |
|   | 0.25 | 3.45**** |
| 6 | 0 | 5.81 |

| Compound of Example No. | Dose of Compound (mmol/kg bodyweight) | Blood Glucose concentration (mmol/liter) 60 minutes after subcutaneous glucose load |
|---|---|---|
| | 0.25 | 3.13**** |
| 7 | 0 | 6.07 |
| | 0.25 | 4.98 |
| 8 | 0 | 7.01 |
| | 0.2 | 3.94**** |
| 9 | 0 | 5.85 |
| | 0.25 | 3.62**** |
| 10 | 0 | 6.32 |
| | 0.2 | 4.26*** |
| 11 | 0 | 7.12 |
| | 0.25 | 5.80*** |
| 12 | 0 | 7.03 |
| | 0.25 | 5.45*** |
| 13 | 0 | 7.46 |
| | 0.2 | 6.06*** |
| 15 | 0 | 7.12 |
| | 0.25 | 5.78*** |
| 16 | 0 | 7.31 |
| | 0.25 | 3.32*** |

**P <0.05
***P <0.01
****P <0.001

We claim:

1. A compound of formula (II) or a pharmaceutically acceptable quaternary ammonium or acid addition salt thereof:

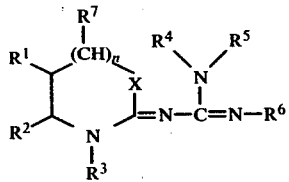

(II)

wherein
X represents oxygen or sulphur;
n represents zero or 1;
$R^7$ represents hydrogen or $C_{1-6}$alkyl;
$R^1$ and $R^2$ are the same or different and represent hydrogen, $C_{1-6}$alkyl, phenyl, benzyl, or $C_{3-6}$cycloalkyl;
$R^3$ represents hydrogen, $C_{1-6}$alkyl, phenyl or benzyl;
$R^4$ represents hydrogen or $C_{1-6}$alkyl;
$R^5$ represents $C_{1-6}$alkyl, phenyl optionally substituted with up to 3 groups selected from halogen, $C_{1-6}$alkyl, and $C_{1-6}$alkoxy; or benzyl optionally substituted with up to 3 groups selected from halogen, $C_{1-6}$alkyl and $C_{1-6}$alkoxy; or $R^4$ and $R^5$ together represent the remaining members of a 5- or 6-membered ring optionally containing an oxygen, sulphur or additional nitrogen atom and being optionally substituted with $C_{1-6}$alkyl, carboxy or $C_{1-6}$alkoxycarbonyl; and
$R^6$ represents phenyl, optionally substituted with up to 3 groups selected from halogen, $C_{1-6}$alkyl, $C_{1-6}$alkoxy, $C_{1-6}$alkanoyl, $C_{1-6}$alkanoyloxy, nitro, hydroxy, amino, substituted amino, carboxy, and $C_{1-6}$alkoxycarbonyl.

2. A compound as claimed in claim 1 wherein n is zero.

3. A compound as claimed in claim 1 wherein $R^7$ is hydrogen and n is one.

4. A compound as claimed in claim 1 wherein $R^1$ and $R^2$ represent hydrogen.

5. A compound as claimed in claim 1 wherein $R^3$ represents hydrogen or $C_{1-6}$alkyl.

6. A compound as claimed in claim 5 wherein $R^3$ represents methyl or ethyl.

7. A compound as claimed in claim 1 wherein $R^4$ and $R^5$ together represent the remaining members of a 5- or 6-membered ring optionally containing an oxygen, sulphur or additional nitrogen atom and being optionally substituted with $C_{1-6}$alkyl, carboxy or $C_{1-6}$alkoxycarbonyl.

8. A compound as claimed in claim 7 wherein $R^4$ and $R^5$ complete a pyrrolidine, piperidine, morpholine, thiomorpholine, piperazine or 4($C_{1-6}$alkyl)piperazine.

9. A compound as claimed in claim 7 wherein the ring is unsubstituted, or substituted with $C_{1-6}$alkyl.

10. A compound as claimed in claim 1 having formula (III) or a pharmaceutically acceptable quaternary ammonium or acid addition salt thereof:

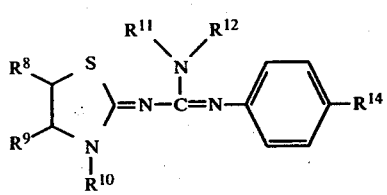

(III)

wherein
$R^8$ and $R^9$ represent hydrogen or $C_{1-6}$ alkyl;
$R^{10}$ represents hydrogen or $C_{1-6}$ alkyl;
$R^{11}$ and $R^{12}$ together represent the remaining members of a 5- or 6-membered ring optionally containing an oxygen or additional nitrogen atom and being optionally substituted with $C_{1-6}$ alkyl; and
$R^{14}$ represents hydrogen, $C_{1-6}$ alkyl or halogen.

11. A compound as claimed in claim 1 wherein $R^4$ and $R^5$ together represent —(CH$_2$)$_4$—, —CH$_2$O(CH$_2$)$_2$—, —(CH$_2$)$_2$O(CH$_2$)$_2$—, —(CH$_2$)NR$_X$(CH$_2$)$_2$—, or —(CH$_2$)$_2$NR$_X$(CH$_2$)$_2$— in which R$_X$ is hydrogen or $C_{1-6}$ alkyl.

12. A compound as claimed in claim 1 selected from the following or their pharmaceutically acceptable quaternary ammonium or acid addition salts thereof:
N-(3-methylthiazolidin-2-ylidene)-N'-phenyl-1-pyrrolidine carboxamidine;
N-(3-methylthiazolidine-2-ylidene)-N'-phenyl-1-piperidine carboxamidine;
N-(3-methylthiazolidin-2-ylidene)-N'-phenyl-1-(4-methylpiperazine)carboxamidine;
N-(3-methylthiazolidin-2-ylidene)-N'-phenyl-1-morpholine carboxamidine;
N-(3-methylthiazolidin-2-ylidene)-N'-(4-methylphenyl)-1-oyrrolidine carboxamidine;
N-(3-methylthiazolidin-2-ylidene)-N'-(4-chlorophenyl)-1-pyrrolidine carboxamidine;
N-(3-ethylthiazolidin-2-ylidine)-N'-phenyl-1-pyrrolidine carboxamidine;
N-(3-methylthiazolidin-2-ylidine)-N'-phenyl-1-thiomorpholine-carboxamidine;
N'-(4-chlorophenyl)-N-(3-methylthiazolidin-2-ylidine)-1-morpholine-carboxamidine;
N'-(4-bromophenyl)-N-(3-methylthiazolidin-2-ylidine)-1-morpholine-carboxamidine;
N'-(3,4-dichlorophenyl)-N-(3-methylthiazolidin-2-ylidine)-1-pyrrolidine carboxamidine;
N,N-diethyl-N'-(3-methylthiazolidin-2-ylidine)-N''-phenylguanidine;

N'-(2,6-dichlorophenyl)-N-(3-methylthiazolidin-2-ylidine)-1-morpholine-carboxamidine;

N-(3-methyloxazolidin-2-ylidene)-N'-phenyl-1-pyrrolidine carboxamidine.

13. A pharmaceutical composition for the treatment of diabetes which comprises a compound, or a pharmaceutically acceptable quaternary or acid addition salt thereof, as claimed in claim 1 together with a pharmaceutical carrier or excipient said compound or salt being present in an amount effective against diabetes.

14. An anti-diabetic composition according to claim 13 in orally or parenterally administrable form or in the form of suppositories.

15. An antidiabetic composition in which the anti-diabetic agent is a compound of claim 12 and is present in an amount effective against diabetes.

16. A method of treating diabetes which comprises administering orally or parenterally to a diabetic host in need thereof an anti-diabetic amount of a composition of claim 13.

17. A method according to claim 16 wherein the composition is in unit dosage form.

* * * * *

Notice of Adverse Decision in Interference

In Interference No. 100,889, involving Patent No. 4,250,173, B. C. C. Cantello, HETEROCYCLIC COMPOUNDS AND PHARMACEUTICAL USE, final judgment adverse to the patentee was rendered Jan. 7, 1983, as to claims 1-17.
[*Official Gazette May 17, 1983.*]